United States Patent [19]
Cella et al.

[11] 4,013,786
[45] Mar. 22, 1977

[54] HAIR CREME RINSES AND HAIR CONDITIONERS CONTAINING HYDROPHOBIC-LIPOPHOBIC PERFLUORINATED COMPOUNDS

[75] Inventors: John A. Cella, Plandone Mills, N.Y.; August Emil Fiebig, Jr., Chicago; Franz J. Pum, Glen Ellyn, both of Ill.

[73] Assignee: Alberto Culver Company, Melrose Park, Ill.

[22] Filed: May 31, 1974

[21] Appl. No.: 474,953

[52] U.S. Cl. .......................... 424/70; 252/DIG. 2; 252/DIG. 13; 252/544; 252/545; 252/546; 252/547; 252/550; 424/DIG. 2; 424/DIG. 4; 424/71; 424/78; 424/170; 424/172; 424/224; 424/311; 424/313; 424/315; 424/317; 424/321; 424/343; 424/362; 424/365

[51] Int. Cl.² ................................ A61K 7/08

[58] Field of Search ............ 424/70, 224, 317, 313, 424/343, 315, DIG. 4; 260/556 F; 252/DIG. 2, DIG. 13, 311, 321

[56] References Cited

UNITED STATES PATENTS

| | | | |
|---|---|---|---|
| 2,732,398 | 1/1956 | Brice et al. | 260/556 F X |
| 2,759,019 | 8/1956 | Brown et al. | 260/556 F |
| 2,803,656 | 8/1957 | Ahlbrecht et al. | 260/556 F |
| 2,809,990 | 10/1957 | Brown | 260/556 F X |
| 2,915,554 | 12/1959 | Ahlbrecht et al. | 260/556 F |
| 3,147,064 | 9/1964 | Brown et al. | 8/116.2 |
| 3,147,066 | 9/1964 | Brown et al. | 8/116.2 |
| 3,217,035 | 11/1965 | Lazerte et al. | 260/556 F |
| 3,245,817 | 4/1966 | Lovness | 106/279 |
| 3,568,685 | 3/1971 | Scott | 424/71 X |
| 3,708,537 | 1/1973 | Groves | 260/556 F |

OTHER PUBLICATIONS

Schwartz et al., vol. 2, *Surface Active Agents and Detergents*, Interscience Publishers, New York, pp. 150–152, (1958).

*Primary Examiner*—Albert T. Meyers
*Assistant Examiner*—Vera C. Clarke
*Attorney, Agent, or Firm*—Wallenstein, Spangenberg, Hattis & Strampel

[57] ABSTRACT

Hair creme rinses and hair conditioners containing distinctly minor proportions of hydrophobic-lipophobic perfluorinated compounds.

12 Claims, No Drawings

HAIR CREME RINSES AND HAIR CONDITIONERS CONTAINING HYDROPHOBIC-LIPOPHOBIC PERFLUORINATED COMPOUNDS

Our invention is directed to improved hair creme rinses and hair conditioners for the treatment of hair on the human head.

It has long been known that the sebaceous glands in the human scalp substantially continuously secrete sebum which acts to keep the hair lubricated, smooth and shiny. It has also long been known that many people suffer from an overproduction of sebum and, as a result, have oily hair. Oily hair readily picks up dust and other particulate matter from the environment which results in the hair becoming soiled and sticky, a situation which requires frequency hair shampooing, commonly as often as every day or every other day, in order to make the hair look clean and presentable.

The secretion products of the sebaceous glands, especially if produced in excess, frequently have an adverse effect on certain hair care products which are applied to the live human hair to impart desirable properties thereto in relation to texture, hold and general appearance. Among such hair treatment products creme rinses and hair conditioners are most generally adversely affected by the sebum or natural oils secreted by the sebaceous glands. In this connection, it may be noted that such creme rinses and hair conditioners commonly contain resins or resinous ingredients, for instance, polyvinylpyrrolidone (PVP). The sebum or natural oils tend to plasticize the resins with the result that the desired properties of the resins are adversely affected, resulting in diminishing or loss of the holding power of the resins. The adverse effect of the sebum or natural oils secreted by the sebaceous glands is not, however, limited only to those creme rinses and hair conditioners which contain resins or resinous materials as ingredients thereof. Creme rinses and hair conditioners which impart to the hair such properties as body, sheen and a soft, silky touch, and which do not contain resins or resinous materials, are also commonly undesirably affected by reasons of the spread of the sebaceous secretions along the hair shaft with the result that the hair becomes oily and sticky, depending upon the amount or extent of such secretions, measured, also, of course, as a function of time. In many instances, it can be observed that resins or other materials deposited on hair speed up the spreading of the sebum along the hair shaft and, so, enhance the adverse effects of excess sebum.

We have found that the incorporation into hair creme rinses and hair conditioners of distinctly minor amounts of certain compounds not only does not adversely affect their effectiveness but, indeed, enhances their effectiveness in that it substantially reduces the excess flow of the sebum or sebaceous secretions by treatment of the hair with the creme rinses and hair conditioners.

The aforementioned chemical compounds which are incorporated into the creme rinses and hair conditioners to produce the creme rinses and hair conditioners of our present invention are hydrophobic-lipophobic perfluorinated compounds which can be represented by the formula $$CF_3-(CF_2)_x-(CH_2)_y-Z$$

where Z is a water or oil solubilizing group of either organic or inorganic character, x is an integer which is generally from 2 to 17, particularly from 7 to 11, and y is an integer of 0 to 4, and said compounds may be anionic, cationic, nonionic or amphoteric, depending upon the nature of the grouping or groupings encompassed by Z. The Z groups may be or may comprise sulfonic, sulfate, phosphate, amide, alkyl-substituted amide, sulfonamido, carboxylic, quaternary ammonium, betainic and similar groups. The hydrophobic-lipophobic perfluorinated compounds are per se known to the art and are identified by trademarks such as FLUORADS (Minnesota Mining and Manufacturing Company) and ZONYLS (E. I. du Pont de Nemours & Company). The water solubility and organic solvent solubility of the aforesaid compounds are, as is known, affected and can be controlled by varying the chain length of the perfluorinated hydrocarbon moiety and by the selection of Z as designated in the above-mentioned formula. It also should be noted in this connection that oily and sticky hair requires more frequent shampooing. It is common knowledge that frequent shampooing dries out the scalp and slightly damages hair. By delaying the flow of sebum along the hair shaft, less often shampooing is necessary, which represents an additional benefit of this invention.

Illustrative examples of the hydrophobic-lipophobic perfluorinated compounds are the following:

(1) $CF_3-(CF_2)_7-SO_3H$
(2) $CF_3-(CF_2)_7-SO_3M$
(3) $CF_3-(CF_2)_7-SO_2-NH-CH_3$
(4) $CF_3-(CF_2)_9-SO_2-N(C_2H_5)-CH_2-COOH$ (M)
(5) $CF_3-(CF_2)_7-SO_2-N(CH_3)-(C_2H_4O)_8H$
(6) $CF_3-(CF_2)_9-SO_2-N(C_2H_5)-C_2H_4-OP(O)(OH)_2$ (M)
(7) $CF_3-(CF_2)_{11}-SO_2-N(CH_3)-CH_2CH_2OSO_3H$ (M)
(8) $CF_3-(CF_2)_9-SO_2-NH-(C_3H_6)N(CH_3)_2$
(9) $CF_3-(CF_2)_7-SO_2-NH-C_2H_4-N^+(C_2H_5)_2-C_2H_4COOH$ (M)
(10) $CF_3-(CF_2)_7-COOH$ (M)
(11) $CF_3-(CF_2)_9-COOC_2H_5$
(12) $CF_3-(CF_2)_7-(CH_2)_y OH$
(13) $CF_3-(CF_2)_7-CO-NH-C_3H_6-N(CH_3)_2$

-continued

| | | |
|---|---|---|
| (14) | $CF_3-(CF_2)_7-CO-NH-C_3H_6-\underset{\underset{C_2H_5}{\mid}}{\overset{\overset{C_2H_5}{\mid}}{N}} \cdot HX$ | (X = organic or inorganic anion, e.g. titrate, tartrate or acetate, Cl, Br, sulphate, phosphate) |
| (15) | $CF_3-(CF_2)_6-CONHC_3H_6{}^+N\underset{\diagdown CH_3}{\overset{\diagup CH_3}{-}}CH_2CH_2COOH$ (M) | |
| (16) | $CF_3-(CF_2)_6-(CH_2)_yOH$ | y = (1 to 4) |
| (17) | $CF_3-(CF_2)_6-(CH_2)_y\overset{\overset{O}{\|}}{O}C(CH_2)_xCH_3$ | x = 1 to 20<br>y = 1 to 4 |
| (18) | $CF_3-(CF_2)_6-(CH_2)_yS(CH_2)_xCOOM$ | y = 1 to 4<br>x - 1 to 20 |
| (19) | $CF_3-(CF_2)_6-(CH_2)_yO-\overset{\overset{O}{\|}}{C}-CH_2$<br>$CF_3-(CF_2)_6-(CH_2)_yO-\overset{\overset{O}{\|}}{C}-\overset{\mid}{C}-OH$<br>$CF_3-(CF_2)_6-(CH_2)_yO-\overset{\overset{O}{\|}}{C}-CH_2$ | y = 1 to 4 |
| (20) | $\begin{matrix} CF_3-(CF_2)_6-(CH_2)_yO \\ \diagdown \\ \diagup \\ CF_3-(CF_2)_6-(CH_2)_yO \end{matrix} \overset{O}{\underset{\|}{P}}-O\ (M)$ | y = 1 to 4<br>M - alkali or $NH_4^+$ |

The aforesaid hydrophobic-lipophobic perfluorinated compounds are effective, in the hair creme rinses and hair conditioners of our present invention, in very low concentrations, as low as 0.05%, by weight of the hair creme rinses and hair conditioners, to of the order of about 1 or 2% or slightly higher. As a general rule, proportions of the order of about 0.1 to 1% are generally adequate, with a good general average being about 0.5 to 1%. The lower limit is determined by the particular efficacy of the specific compounds in selected hair creme rinses and hair conditioners, whereas the upper limit, not in excess of 10%, is usually governed by somewhat similar considerations except that, generally speaking, no more should be used than is necessary and, in addition, it is desirable not to exceed the solubility or ready dispersibility limits of the compound in the particular hair creme rinses and hair conditioners involved, while maintaining homogeneity therein.

The compositions, in their particularly advantageous embodiments, also contain, in addition to the aforesaid perfluorinated compounds, minor proportions of generally water-soluble non-perfluorinated cationic surfactants, in proportions generally in the range of about 0.1 to about 2.5%, more particularly about 0.2 to 1.7%. Such cationic surfactants are well known in the art and include, among others, quaternary ammonium compounds but are in no way limited thereto. Illustrative examples thereof are dimethyl distearyl ammonium chloride, cetyl trimethyl ammonium chloride, trimethyl palmityl ammonium bromide, stearyl dimethyl benzyl ammonium chloride, cetyl diethyl benzyl ammonium chloride and cetyl pyridinium chloride.

The creme rinses and hair conditioners are generally in the form of aqueous compositions which may contain a lower molecular weight water-soluble aliphatic organic solvent, generally an alcohol such as ethanol or isopropanol, but which may also be carbitol or acetone, such organic solvents as may be present generally being present in minor proportions, generally up to about 10% based on the weight of the finished compositions.

In general, the water content is present in major proportion of the finished compositions, commonly about 70% to about 90% based on the weight of the composition. The pH of the compositions of the present invention will generally vary from 2.5 to 8 but, in the usual case, the pH is most desirably on the acid side and, in the particularly advantageous embodiments, the pH will ordinarily range from about 4.7 to about 6.

The following examples are illustrative but in no way limitative of the invention since many other hair creme rinses and hair conditioners can readily be made in light of the guiding principles and teachings contained herein. All percentages listed are by weight, unless otherwise specifically stated.

EXAMPLE 1

| Creme Rinse (to be left on the hair) | |
|---|---|
| Water | 83.20 |
| Antifoam AF[1] | 0.05 |
| Arquad 2HT[2] (10% active) | 15.50 |
| Arquad S50[3] | 0.10 |
| Compound of structure 6 | 1.00 |
| Perfume | 0.15 |
| | 100.00% |

[1]Dimethylpolysiloxane, silica, stearate emulsifiers, sorbic acid, water
[2]Dimethyl Di(Hydrogenated Tallow) Ammonium Chloride
[3]Trimethylsoyammonium Chloride In the preparation of the creme rinse of this Example 1, it is convenient to disperse the Antifoam AF in the water, with stirring, and then add the Arquad 2HT. The perfume is mixed with the Arquad S50 and the resulting mixture is added to the initial mixture under conditions of stirring. The compound of structure 6 is then added, with stirring, over a suitable period of time, for instance, of the order of about 20 minutes.

Mixing procedures for other creme rinses and hair conditioners of the present invention, illustratively disclosed in the following Examples, will be apparent to those skilled in the art.

EXAMPLE 2

| Creme Rinse (leave on) | |
|---|---|
| Soft Water | 74.85 |
| Arquad 2HT (10% active) | 17.00 |
| Ethanol | 7.00 |
| Compound of structure 22 | 1.00 |
| Perfume | 0.15 |
| | 100.00% |

EXAMPLE 3

| Creme Rinse (leave on) | |
|---|---|
| Water | 78.85 |
| Antifoam AF | 0.05 |
| Arquad 2HT (10% active) | 6.50 |
| Gafquat 750[4] | 4.00 |
| Ethanol | 10.00 |
| Compound of structure 6 | 0.50 |
| Perfume | 0.10 |
| | 100.00% |

[4]Quaternized Vinylpyrrolidone Copolymer

EXAMPLE 4

| Creme Rinse (leave on) | |
|---|---|
| Soft Water | 83.75 |
| Arquad 2HT (10% active) | 15.00 |
| Arquad S50 | 0.10 |
| Compound of structure 20 | 1.00 |
| Perfume | 0.15 |
| | 100.00% |

EXAMPLE 5

| Creme Rinse | |
|---|---|
| Soft Water | 84.35 |
| Span 80[5] | 1.20 |
| Tween 80[6] | 0.20 |
| Mineral Oil | 2.60 |
| Lauryl Alcohol | 2.00 |
| Variquat 124-137[7] | 6.40 |
| Protein (Wilson's WSPA-200) | |
| Aqua-Pro | 2.00 |
| Perfume | 0.25 |
| Compound of structure 7 | 1.00 |
| | 100.00% |

[5]Sorbitan Mono-oleate
[6]Polyoxyethylene (20) Sorbitan Mono-oleate
[7]Cetyl Trimethyl Ammonium Chloride

EXAMPLE 6

| Creme Rinse | |
|---|---|
| Soft Water | 90.50 |
| Span 80 | 1.00 |
| Tween 60 | 0.30 |
| Mineral Oil | 1.00 |
| Cetyl Alcohol | 2.00 |
| Varisoft SDC 25[8] | 4.00 |
| Compound of structure 6 | 1.00 |
| Perfume | 0.20 |
| | 100.00% |

[8]Stearyl Dimethyl Benzyl Ammonium Chloride

EXAMPLE 7

| Creme Rinse | |
|---|---|
| Soft Water | 88.07 |
| Cellosize QP4400[9] | 1.00 |
| Alcasan 7 LUF[10] | 1.50 |
| Ethanol | 7.00 |
| Dowicil 200[11] | 0.20 |
| Phosphoric Acid | 0.03 |
| Compound of structure 22 | 2.00 |
| Perfume | 0.20 |
| | 100.00% |

[9]Hydroxyethyl Cellulose
[10]Alkyl Dimethyl Benzyl Ammonium Chlorides
[11]1-(3-Chloroallyl)-3,5,7-Triaza-1-Azoniaadamantane

EXAMPLE 8

| Hair Conditioner | |
|---|---|
| Soft Water | 90.25 |
| Methocel 65 HG 400 cps[12] | 1.35 |
| Alcasan 7 LUF | 2.00 |
| Ethanol | 5.00 |
| Methyl Paraben[13] | 0.10 |
| Phosphoric Acid | 0.15 |
| Compound of structure 6 | 1.00 |
| Perfume | 0.15 |
| | 100.00% |

[12]Hydroxypropyl Methyl Cellulose
[13]Para-Hydroxy Methyl Benzoate

EXAMPLE 9

| Hair Conditioner | |
|---|---|
| Soft Water | 85.85 |
| Methocel 65 HG 400 cps | 1.20 |
| Chemadene 300[14] | 3.00 |
| Ethanol | 7.00 |
| Methyl Paraben | 0.15 |
| Citric Acid | 2.00 |
| Compound of structure 19 | 0.60 |
| Perfume | 0.20 |
| | 100.00% |

[14]Amphoteric Surfactant

EXAMPLE 10

| Hair Conditioner | |
|---|---|
| Soft Water | 90.62 |
| Cellosize QP 4400 | 0.80 |
| Alcasan 7 LUF | 2.20 |
| Ethanol | 5.00 |
| Dowicil 200 | 0.20 |
| Phosphoric Acid | 0.03 |
| Compound of structure 11 | 1.00 |
| Perfume | 0.15 |
| | 100.00% |

We claim:

1. A composition, for treating human live hair, selected from the class consisting of creme rinses and hair conditioners having an aqueous carrier, which includes, as an ingredient thereof, a hydrophobic-lipophobic compound of anionic, cationic, nonionic or amphoteric character corresponding to the formula $$CF_3-(CF_2)_x-(CH_2)_y-Z$$

where Z comprises a member selected from the class consisting of a water-solubilizing group and an oil-solubilizing group, $x$ is an integer from 2 to 17, and $y$ is an integer from 0 to 4, said compound being present in proportions, based on the weight of the composition, in the range of about 0.05% to not in substantial excess of the solubility or ready dispersibility of said compound in the composition and not in excess of 10%.

2. The composition of claim 1, in which the proportions of said compound are in the range of about 0.5% to about 1%.

3. The composition of claim 1, containing from about 70 to 90% by weight of water in said composition.

4. The composition of claim 3, which contains up to about 10% by weight of a lower molecular weight aliphatic alcohol.

5. The composition of claim 1, in which, in the hydrophobic-lipophobic compound, $x$ is 7 to 11.

6. The composition of claim 5, in which Z is a member selected from the class consisting of a sulfonic, sulfate, carboxyl, phosphate and quaternary ammonium group.

7. The composition of claim 5, in which Z is a cationic radical.

8. The composition of claim 1, which also includes from about 0.1% to about 2.5% of another water-soluble cationic surfactant.

9. The composition of claim 5, which also includes from about 0.1% to about 2.5% of another water-soluble cationic surfactant.

10. The composition of claim 7, which also includes from about 0.2 to about 1.7% of a water-soluble quaternary ammonium chloride.

11. A method of treating human live hair which comprises applying to said hair an effective amount of a composition selected from the class consisting of creme rinses and hair conditioners having an aqueous carrier, said composition including, as an ingredient thereof, a hydrophobic-lipophobic compound of anionic, cationic, nonionic or amphoteric character corresponding to the formula

where Z comprises a member selected from the class consisting of a water-solubilizing group and an oil-solubilizing group, $x$ is an integer from 2 to 17, and $y$ is an integer from 0 to 4, said compound being present in proportions, based on the weight of the composition, in the range of about 0.05% to not in substantial excess of the solubility or ready dispersibility of said compound in the composition and not in excess of 10%.

12. The method of claim 11, in which the composition also includes from about 0.1 to about 2.5% of another water-soluble cationic surfactant.

* * * * *